Figure 1:
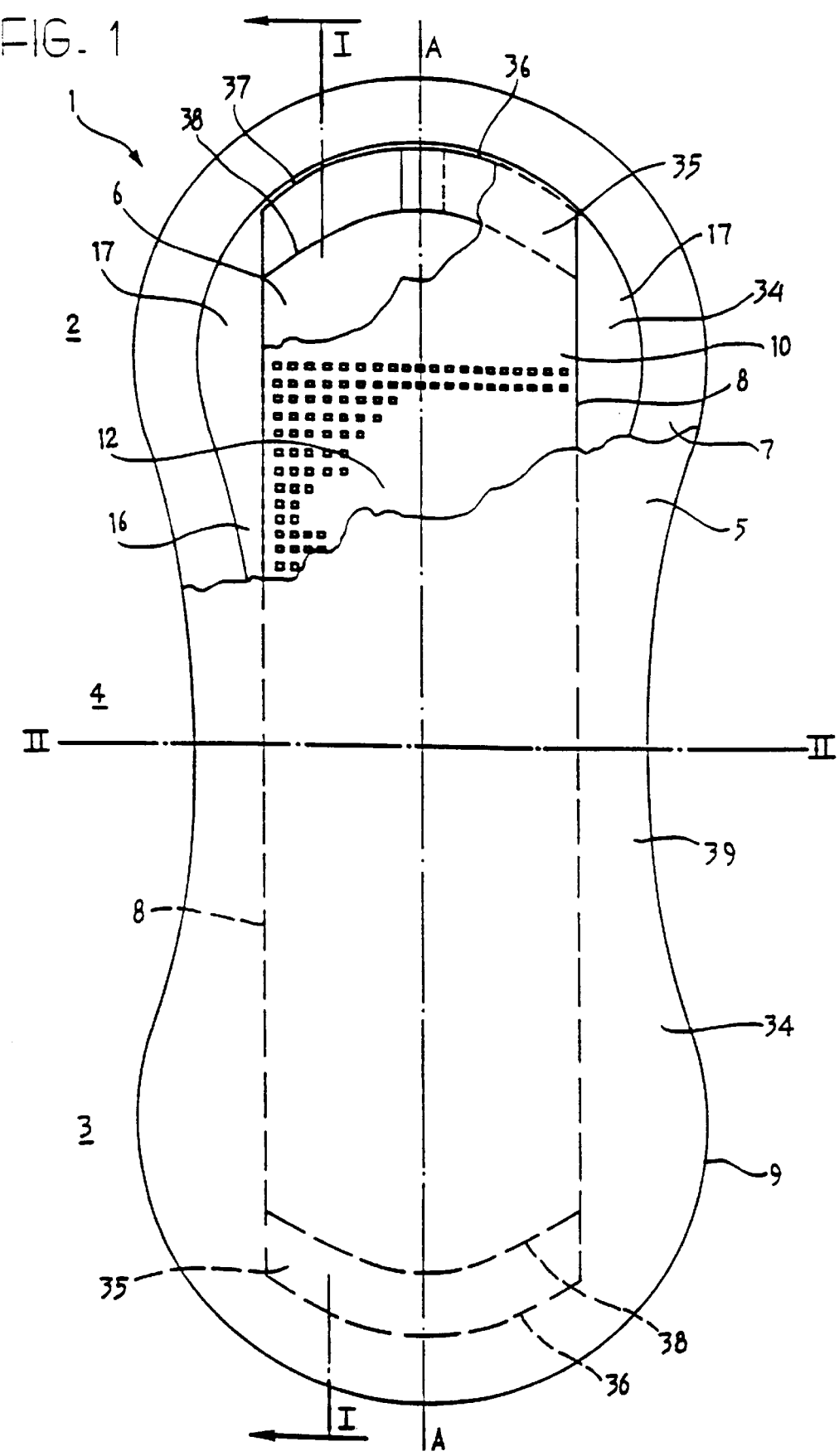

United States Patent

Palumbo

[11] Patent Number: 6,118,042
[45] Date of Patent: Sep. 12, 2000

[54] ABSORBENT ARTICLE WITH CONTROLLED DISTRIBUTION OF LIQUID

[75] Inventor: Gianfranco Palumbo, Pescara, Italy

[73] Assignee: The Procter & Gamble Company, Cincinnati, Ohio

[21] Appl. No.: 08/704,642

[22] PCT Filed: Mar. 13, 1995

[86] PCT No.: PCT/EP95/00931

§ 371 Date: Dec. 23, 1996

§ 102(e) Date: Dec. 23, 1996

[87] PCT Pub. No.: WO95/24878

PCT Pub. Date: Sep. 21, 1995

[30] Foreign Application Priority Data

Mar. 15, 1994 [IT] Italy .................................. T094A0180

[51] Int. Cl.$^7$ .............................. A61F 13/15; A61F 13/20
[52] U.S. Cl. ............................................................ 604/368
[58] Field of Search ........................... 604/368, 378–382, 604/385.1

[56] References Cited

FOREIGN PATENT DOCUMENTS 83 03051  9/1983  WIPO.

*Primary Examiner*—Ronald Stright
*Assistant Examiner*—Ki Yong O
*Attorney, Agent, or Firm*—Matthew P. Fitzpatrick; Jeffrey V. Bamber

[57] ABSTRACT

A disposable sanitary towel (1) comprising an upper layer (5) which is permeable to liquids, a lower impermeable layer (7) and an absorbent member (6) is provided with an intermediate layer (10) located between the upper layer (5) containing the absorbent member (6) and extending around the longitudinal side edges and end edges of the absorbent member (6) so as to distribute the liquid received and to prevent the loss of liquid from the edges of the absorbent member (6).

6 Claims, 7 Drawing Sheets

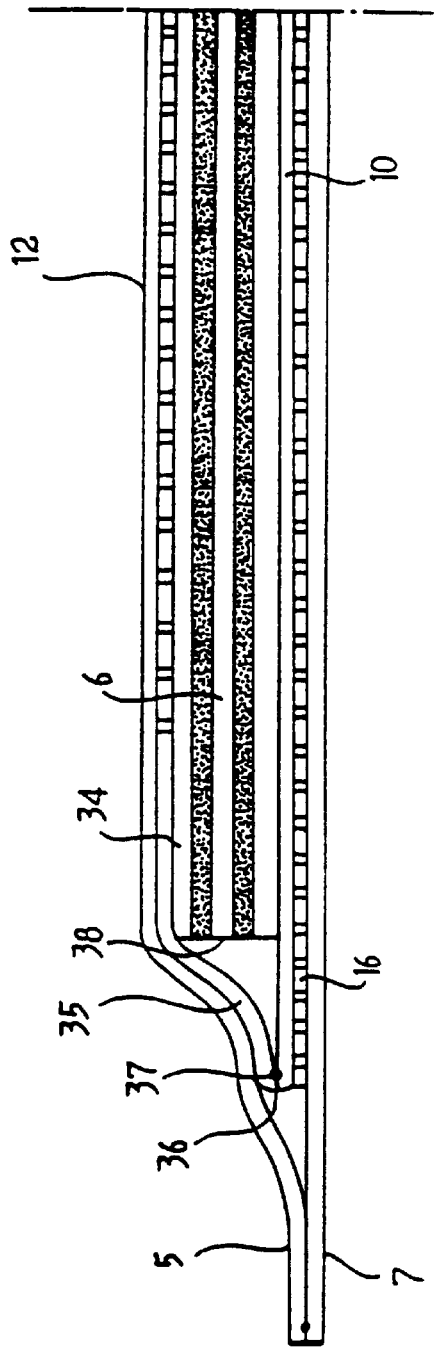
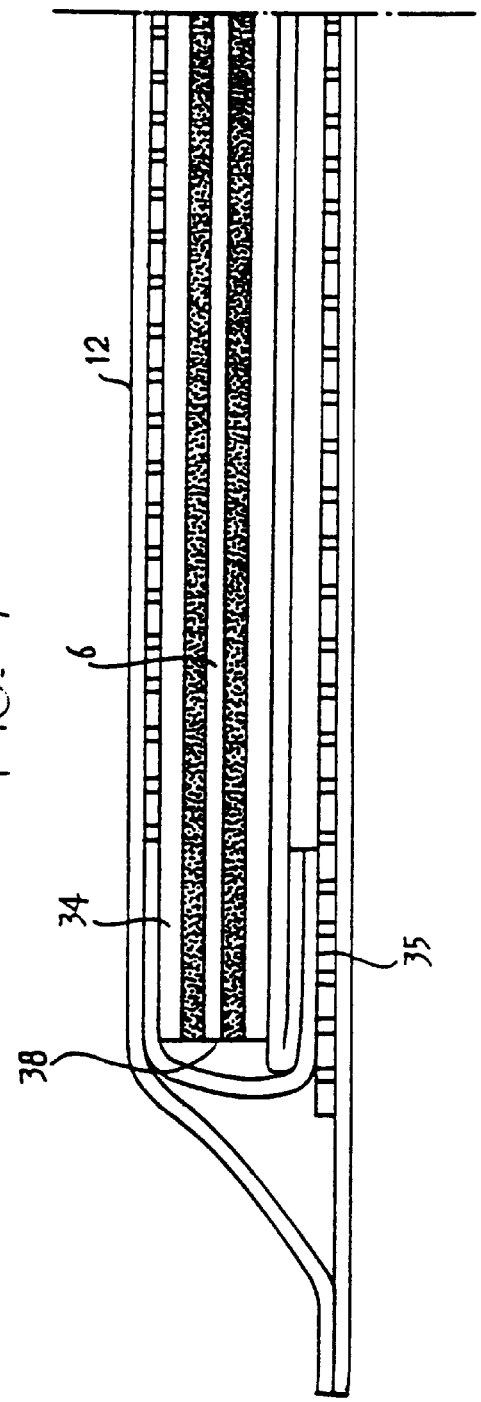

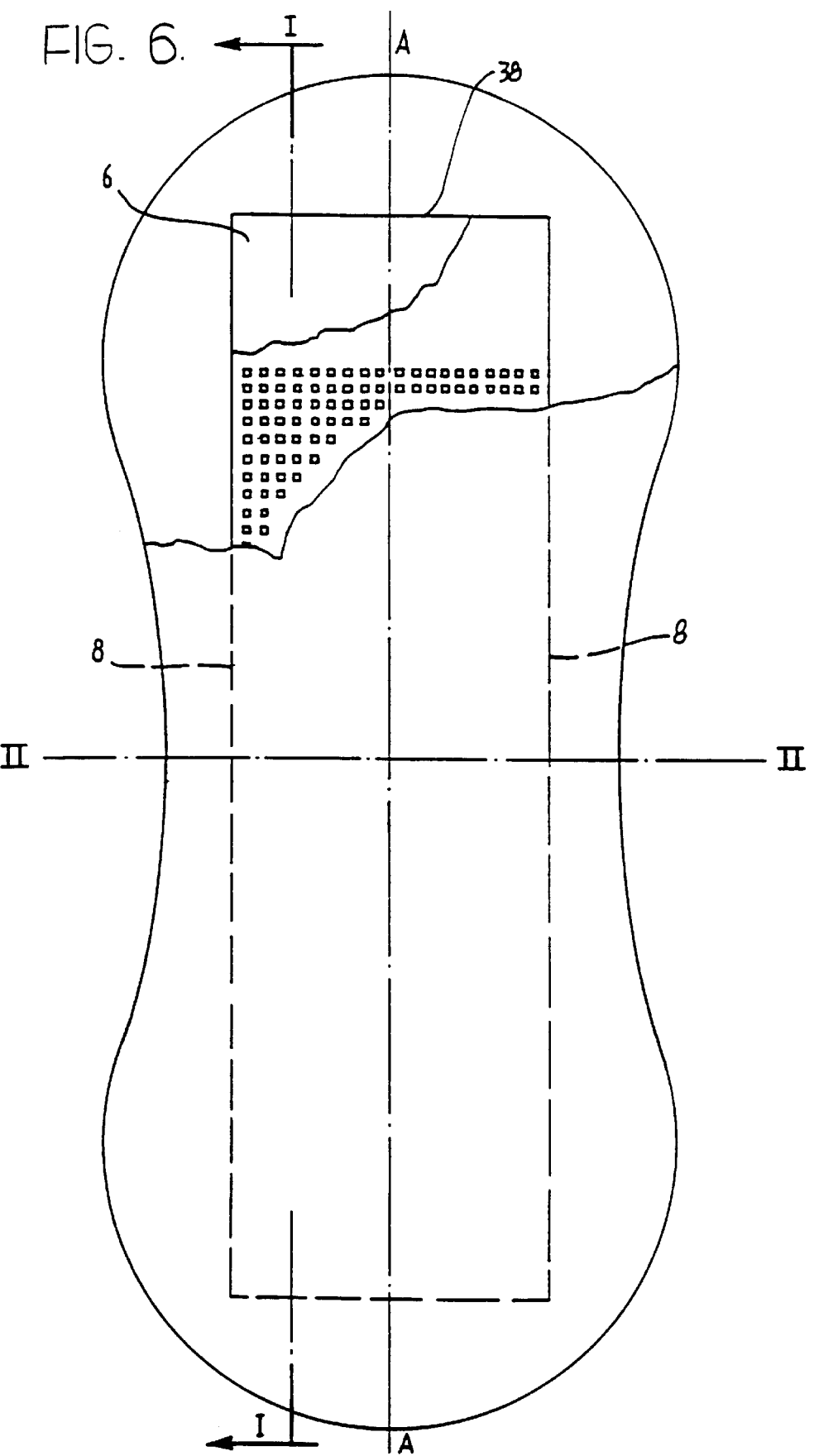

ABSORBENT ARTICLE WITH CONTROLLED DISTRIBUTION OF LIQUID

This invention relates to an absorbent article, for example a sanitary towel, generally comprising an upper layer which is permeable to liquids, a lower layer which is impermeable to liquids and an absorbent member placed between the two.

More particularly the invention relates to a sanitary towel whose structure comprises one or more layers intended to control the distribution of liquid which is deposited on the surface of the upper layer which faces the body of the female user.

Preferred configurations of the invention comprise an absorbent member which contains hydrogelling absorbent material as a component, preferably as a principal component.

Sanitary towels which have an upper layer which is permeable to liquids, an impermeable lower layer and an absorbent member located between the two containing hydrogelling absorbent material are known in the prior art.

U.S. Pat. No. 5,009,653 describes a sanitary towel comprising an upper layer which is permeable to liquids, a lower layer which is impermeable to liquids and an absorbent member located between the two, the absorbent member comprising a layered structure formed of two outer layers of air-laid wadding and a central layer of hydrogelling absorbent material.

A layer to take up liquid formed by a non-woven fabric comprising 70% rayon and 30% polyester fibre is located between the upper layer and the absorbent member and is designed to improve the lateral distribution of liquid passing through the upper layer.

The lateral distribution of liquid in the take-up layer increases the surface area of the absorbent member to which the released liquid has access, but on the other hand there is the possibility that the liquid may migrate to the edges of the sanitary towel, and may therefore soil and stain the intimate garments of the user under certain conditions of use.

Patent EP-A-257280 describes a composite covering layer for an absorbent article such as a sanitary towel in which a perforated substantially hydrophobic polymer film of thickness less than 0.762 mm having a total open area equal to at least 35% is located above a layer of non-woven fabric and fixed thereto, the openings in the first layer being of insufficient size to permit the passage of a 1% saline solution under the effect of gravity alone, while the second layer has a capillary structure such as to permit a vertical rise of 1% saline solution of less than 12.7 mm after 15 minutes.

The absorbent article comprises an absorbent member having a composite two layer structure, in particular an upper low density layer formed of cellulose fibres and a lower layer comprising a highly condensed mixture of cellulose fibre and superabsorbent material.

The underside of the absorbent member is attached to a sheet of polyethylene which extends to the lateral edges of the absorbent member to prevent fluid passing from the base and the sides of the absorbent member to the user's garments. It is considered that the composite covering layer permits liquid to flow in one direction in order to ensure improved cleanliness with regard to flows of liquid, and it is also considered that the said layer shows very little diffusion properties, that is a low capacity for the transmission of liquid in a lateral direction.

There therefore remains the problem of attempting to avoid the disadvantages of an intermediate layer which is completely permeable to liquids, while at the same time retaining the capacity to distribute the liquid received to zones of the absorbent member outside the take-up area.

PCT application Ser. No. PCT/US93/08597 describes a sanitary towel comprising an upper layer which is permeable to liquids, a lower impermeable layer and an absorbent member provided with an intermediate layer located between the upper layer and the absorbent member and configured in such a way as to extend around the lateral edges of the absorbent member itself.

The intermediate layer is capable of distributing the liquid received and also prevents loss of liquid from these lateral edges, being substantially impermeable at the lateral edges of the absorbent. However, it has now been discovered that, for example under particularly severe conditions of use, fluid losses can occur from the two ends of the absorbent member.

It is therefore one object of the invention to provide a sanitary towel having a layered structure which is capable of controlling the liquid released onto the surface of the said sanitary towel facing the body of the female user.

Another object of the invention is to provide a sanitary towel having an absorbent member located between a lower layer which is impermeable to liquids and an upper layer which is permeable to liquids onto which liquid is released, in which an intermediate layer located between the upper layer and the absorbent member distributes the liquid released onto the surface of the absorbent member facing the body of the female user, but is configured in such a way as to prevent losses of liquid from the edges of the absorbent to the user's clothing.

Another object of the invention is to provide a sanitary towel in which an intermediate layer located between the upper layer and the absorbent member distributes the liquid released onto the surface facing the body of the female user of the said absorbent member, the said intermediate layer extending around the lateral edges of the absorbent member at least along its central portion so that the liquid is allowed to diffuse at least along the internal surface of the said intermediate layer around the longitudinal lateral edges of the absorbent member.

Accordingly, the invention is to provide an absorbent article, for example a sanitary towel having the characteristics specifically described in the claims which follow. This involves the use of an intermediate layer configured in such a way as to prevent losses of liquid from both the lateral edges and the end edges of the absorbent member to the user's clothing.

Preferably, the sanitary towel has an upper layer which is permeable to liquids, a lower layer which is impermeable to liquids and an absorbent member located between the two, the said sanitary towel also comprising a hydrophilic intermediate layer located between the upper layer and the absorbent member, in which the absorbent member comprises a layered structure in which the density of the respective layers decreases from the upper layer to the lower layer.

Figure 2:
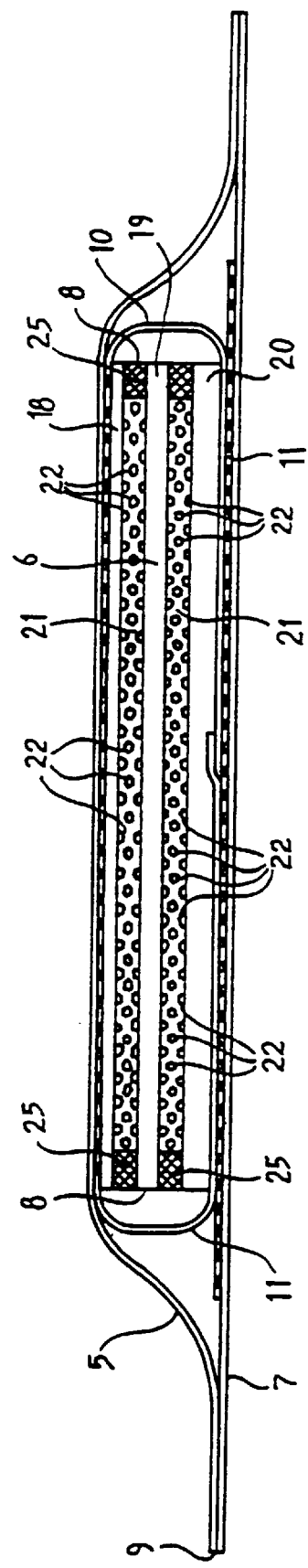
Figure 4:
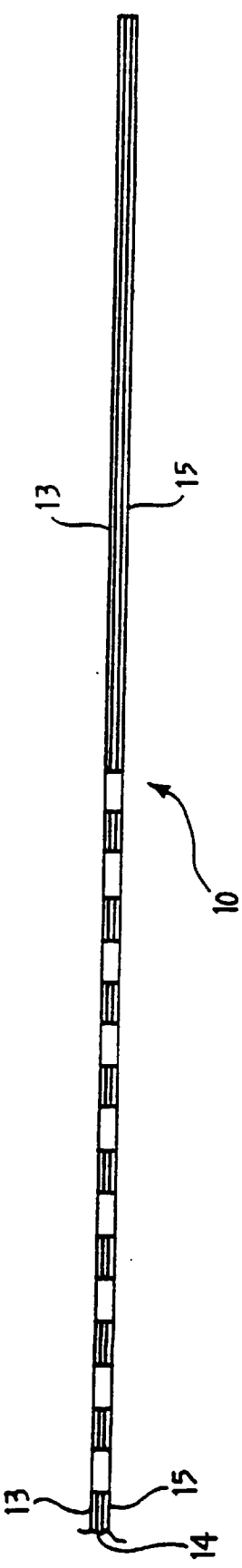
Figure 5:
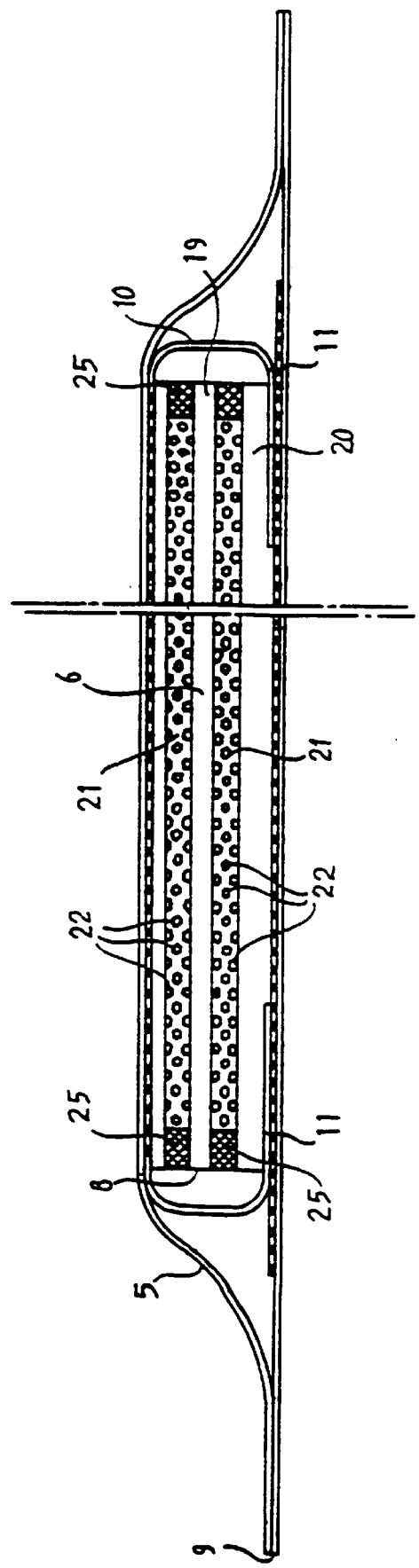

The invention will now be described purely by way of a non-restrictive example with reference to the appended drawings, in which:

FIG. 1 is a plan view of a sanitary towel constructed according to this invention, seen from the side which is designed to be away from the user, FIG. 2 is a view in cross-section of the absorbent along the line II—II in FIG. 1, FIG. 3 is a view in cross-section of the absorbent along the line I—I in FIG. 1, FIG. 4 is a view in partial cross-section of a preferred configuration for the intermediate layer contained within the absorbent according to this invention, FIG. 5 is a view in cross-section of an alternative configuration of an absorbent according to this invention, FIG. 6 is a plan view of an alternative configuration of the sanitary towel constructed according to this invention, seen from the side designed to be away from the user, FIG. 7 is a view in cross-section of the absorbent along line I—I in FIG. 5.

Figure 8A:
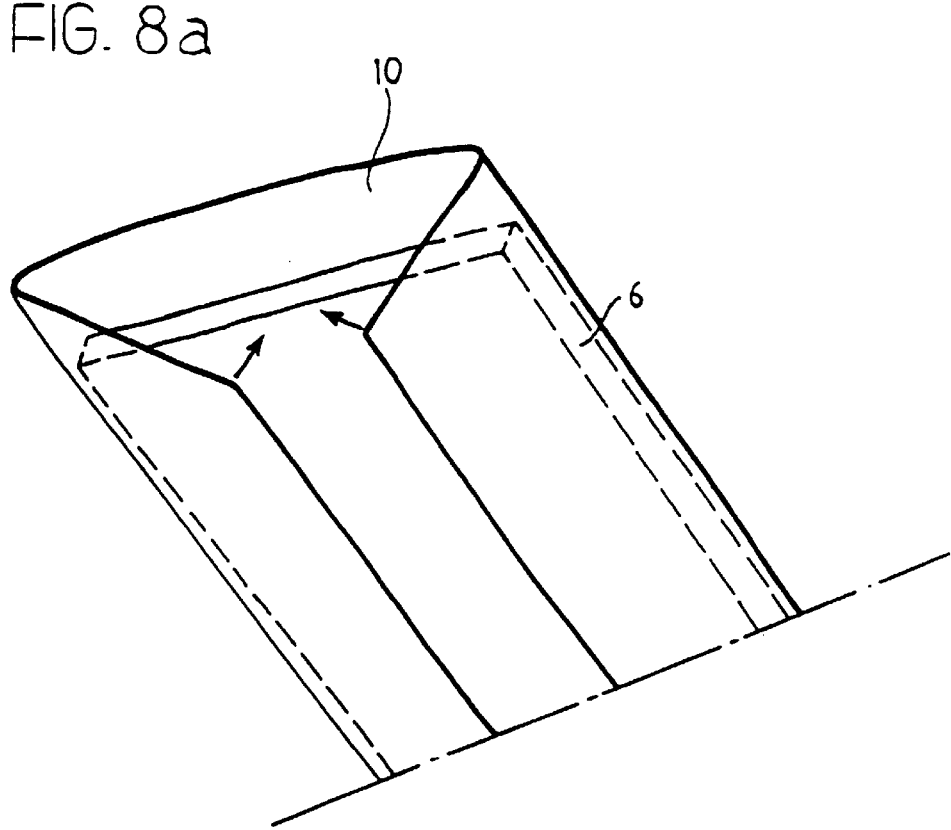
Figure 8B:
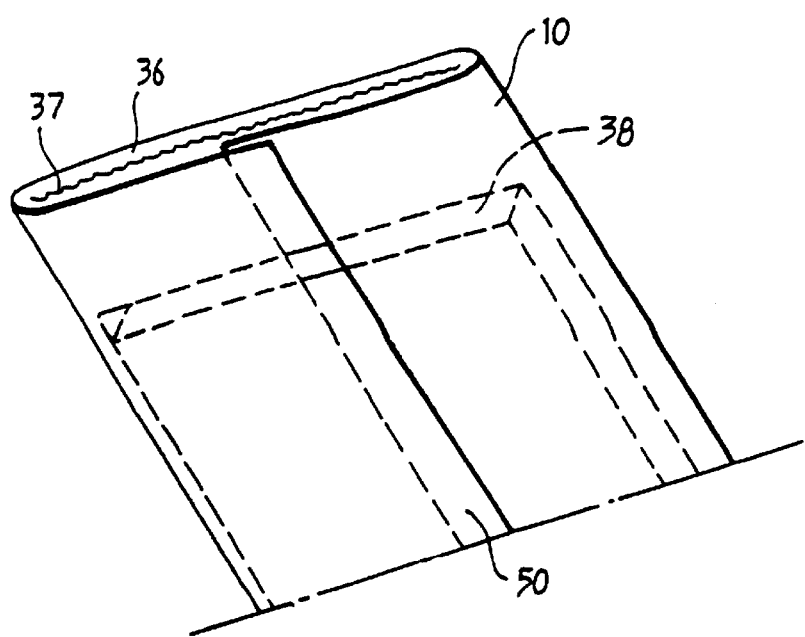
Figure 9A:
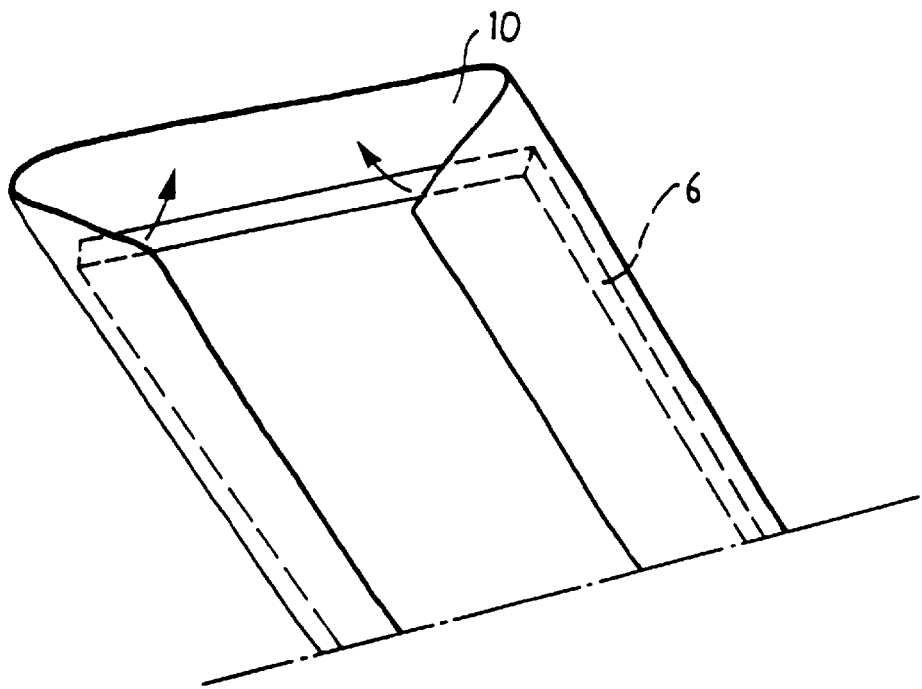
Figure 9B:
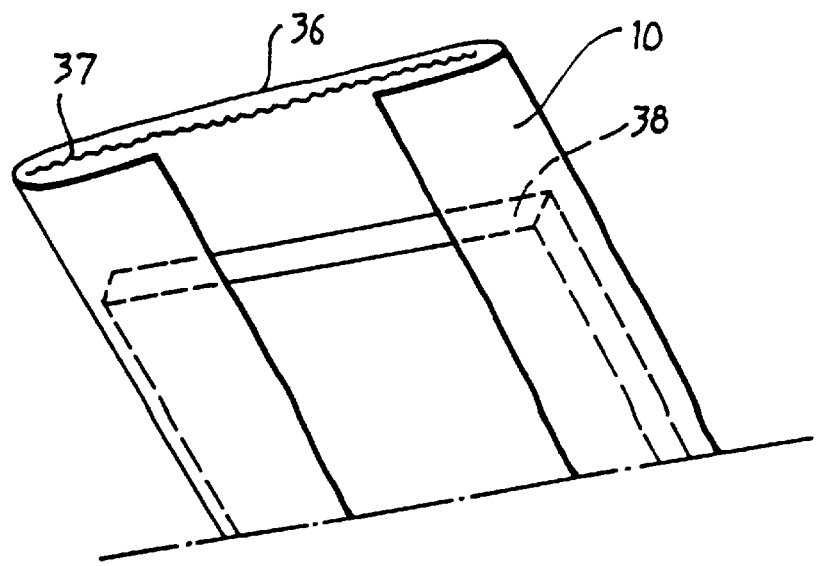

FIGS. 8a and 8b show diagrammatically two successive stages in the manufacture of an absorbent article according to the invention, having an intermediate layer with overlapping longitudinal edges, and FIGS. 9a and 9b are corresponding drawings for an article having an intermediate layer with overlapping longitudinal edges.

This invention relates to disposable absorbent articles and more particularly to sanitary towels for women which are worn externally in direct contact with the body in the vulvar region of the user and whose function is to absorb body fluids, which are then disposed of after a single use.

This invention is not however restricted to sanitary towels alone, but is also applicable to other disposable absorbent articles, such as e.g. panty liners and the like.

The disposable sanitary towel illustrated in FIGS. 1, 2 and 3 represents a preferred embodiment of an absorbent article constructed in accordance with this invention.

FIG. 1 illustrates a sanitary towel 1 constructed in accordance with this invention with a portion of the structure removed to reveal its construction with greater clarity. In particular it shows the upper side of the absorbent which when in use is in direct contact with the body of the female user.

FIG. 1 shows an anterior region 2, a posterior region 3 and a central region 4 lying between the two. It also shows a longitudinal axis AA' and a transverse axis corresponding to section line II—II.

The absorbent comprises an upper layer 5 which is permeable to liquids, which is intended to come into direct contact with the user's body, an absorbent member 6 and a lower layer 7 which is impermeable to liquids.

In the configuration illustrated the absorbent is shaped so as to have greater width in the two anterior 2 and posterior 3 regions, thus being narrower in the central region 4. As is known, this shape provides a better fit for the anatomy of the user. Absorbent member 6 has a rectangular shape with its ends 38 rounded and its lateral longitudinal edges 8 straight and parallel to each other, and is characterised by a width which is slightly less than the minimum width of the absorbent corresponding to central zone 4. In absorbent 6 there is a central zone 39 and two end zones 34, broadly corresponding to central region 4 and anterior 2 and posterior 3 regions of absorbent 1 respectively.

Upper layer 5 which is permeable to liquids and lower layer 7 which is impermeable have the same shape and size corresponding to the external shape of the entire absorbent and are joined together, e.g. by means of a line of gluing or heat welding, along at least the external perimeter 9 of the absorbent.

Upper layer 5 which is permeable to liquids must permit the liquid to pass rapidly through its thickness to the underlying structure. It may be constructed in various ways known in the prior art, e.g. from non-woven fabric, and a perforated polymer film which is permeable to liquids, but which is not absorbent, is nevertheless preferred.

In a preferred configuration of this invention the surface of permeable upper layer 5 facing the body of the user is hydrophilic, particularly where the said upper layer 5 is constructed using perforated polymer film.

The hydrophilic surface ensures faster passage of the liquid through upper layer 5 to the underlying absorbent structure and also reduces the possibility that part of the liquid will flow onto the surface of the upper layer.

The surface of permeable upper layer 5 facing the body may be made hydrophilic by treatment with a surfactant, applied e.g. by spraying or by means of a roller.

As an alternative the surfactant may be incorporated directly in the material from which permeable upper layer 5 is formed.

Absorbent member 6 is covered by an intermediate layer 10 which covers the surface facing the body of the user, lateral longitudinal edges 8 of absorbent member 6, by means of the two longitudinal marginal portions 11, corresponding at least to central region 4 of absorbent 1, and the end edges 38 by means of the two end zones 35. Preferably, as illustrated in FIG. 2, intermediate layer 10 comprises longitudinal marginal portions 11 of such as size as to completely surround absorbent member 6 overlapping partly above it, on the side of the absorbent member which faces the intimate garments.

As illustrated in FIGS. 1 and 3, intermediate layer 10 is longer than absorbent member 6 and its end edges 36 project beyond the end edges 38 of the absorbent member itself.

At end edges 36 the overlapping portions of intermediate layer 10 are welded together, e.g. by means of a line of adhesive 37, as illustrated in FIGS. 1 and 3, thus completely enclosing absorbent member 6 within intermediate layer 10.

Intermediate layer 10 is substantially impermeable to liquids along longitudinal marginal portions 11 which surround the lateral longitudinal edges 8 and at least part of the surface facing the intimate clothing of absorbent member 6, and in the vicinity of the two end zones 35 which correspond to the two ends 34 of absorbent member 6.

The said intermediate layer 10 comprises a portion 12 which is substantially permeable to liquids corresponding to at least part of the surface of absorbent member 6 facing the body of the user. FIG. 1 shows this permeable portion 12 arranged symmetrically with respect to the line II—II, which coincides with the transverse axis of absorbent 1 and is located in the central zone 39 of absorbent member 6.

Intermediate layer 10 is characterised by being substantially voluminous, in excess of 5 $cm^3/g$, preferably in excess of 7 $cm^3/g$, with a good capacity for capillary diffusion of the liquid and a low absorption capacity.

The capillary diffusion capacity and absorption capacity of the material forming the intermediate layer are evaluated by means of a "Horizontal diffusion test" and a "Free absorption test", both of which are performed on rectangular samples of the material 80 mm long and 25.4 mm wide, using a saline solution of 0.9% by weight.

For each test the values obtained represent the mean of the values measured for three identical samples.

Horizontal diffusion test

Equipment called a "Demand wettability tester" illustrated in "Absorbency", edited by Pronoy K. Chatterjee and published by Elsevier Science Publishers B. V., 1985 ed., page 62, with reference to B. M. Lichstein, "INDA Technical Symposium", U.S.A., 1974, page 129, is used.

The test is performed by placing a sample of material having the specified dimensions on a horizontal test plate with one end corresponding to the hole through which the liquid is released with a hydrostatic head of effectively zero.

The time in seconds required for the liquid to reach the other end of the sample, covering the distance of 80 mm, is measured.

Free absorption test

The sample of specified dimensions is weighed and then floated on the surface of the liquid. The surface of the material facing the surface of the liquid is the contact surface in use. The sample is left in the liquid for one minute, and then lifted up by one end using tweezers and allowed to drip for one minute, and is then weighed again. The difference between the initial weight and the final weight represents the quantity of liquid freely absorbed by the sample under test.

The material comprising intermediate layer 10 shall have a capillary diffusion time, measured by the "Horizontal diffusion test", of less than 150 seconds, and a free absorption capacity, measured according to the "Free absorption test", of less than 1 g, and preferably less than 0.5 g.

Use of the coating structure for sanitary hygiene products described in patent EP-B-207904 in the name of the applicant, which is made hydrophilic by means of suitable treatment, has proved to be particularly preferred.

This structure, which is illustrated in particular in FIG. 4, is generally perforated and comprises an upper layer 13 consisting of a non-woven fabric, an intermediate layer 14 consisting of a polymer film and a lower level 15 consisting of a non-woven fabric. The three layers are joined together to form a structure having a thickness of between $200\mu$ and $700\mu$.

In a preferred embodiment of this invention the structure is perforated, and therefore rendered permeable to liquids, only in portion 12 of the said intermediate layer 10, while marginal longitudinal portions 11, which cover longitudinal lateral edges 8 and at least part of the surface of absorbent member 6 facing the intimate clothing, and the two end zones 35, which correspond to the two ends 34 of absorbent member 6, are free of holes and therefore substantially impermeable.

The fibres comprising the non-woven fabric in the upper 13 and lower 15 layers of the layered structure forming intermediate layer 10 are of the hydrophilic type, e.g. rendered such by suitable treatment with surfactants before formation of the said structure.

Preferably the outer surface of said intermediate layer 10, which in this case corresponds to the upper fibrous layer 13 of the layered structure, is hydrophilic only in portion 12 which is substantially permeable to liquids, while the other parts of the outer surface of intermediate layer 10 are hydrophobic, e.g. being rendered such by means of surface treatment subsequent to formation of the said structure.

In use the layered structure is capable of receiving and rapidly transmitting liquid through the holes in permeable portion 12 from the overlying permeable upper layer 5 to absorbent member 6 beneath.

The highly voluminous character of intermediate layer 10 isolates upper permeable layer 5 from the surface of absorbent member 6, helping to keep the surface of the absorbent which faces the body of the user dry while in use.

Unperforated longitudinal marginal portions 11 of intermediate layer 10 prevent losses of liquid which might occasionally occur from longitudinal lateral edges 8 of absorbent member 6 when the sanitary towel is subjected to normal pressures of use.

The bonds between the overlapping portions of intermediate layer 10 corresponding to end edges 38 of each end zone 35, provided e.g. by means of lines of adhesive 37, prevent the loss of liquid which might occur from ends 34 of absorbent member 6 under particularly severe conditions of use, thus making it possible to derive maximum advantage from the absorption capacity of absorbent member 6, including involvement of the said ends 34.

The end zones 35 of intermediate layer 10 correspond to the ends 34 of absorbent member 6 and are not therefore designed to receive the liquid which in use is instead typically released in the approximate vicinity of the centre of central zone 39 of the said absorbent member. As the said end zones 34 are unperforated and therefore impermeable to liquids these are capable of insulating the upper surface of the absorbent from backflows of liquid which might occur at the ends 34 of absorbent member 6.

The capillary diffusion capacity of the two upper 13 and lower 15 fibrous layers, together with the low liquid absorption capacity, result in some of the liquid received through overlying upper layer 5 being transmitted by capillary within the said fibrous layers far from the area in which the said liquid is initially received, typically the centre of permeable portion 12, so that it is diffused in both a longitudinal and transverse direction.

In this way the surface of intermediate layer 10 across which the liquid passes towards underlying absorbent member 6 is increased, with the advantage of providing a greater extent of the said absorbent member to absorb the liquid.

Also the liquid migrating along intermediate layer 10 in a transverse direction is transported beyond lateral longitudinal borders 8 of absorbent member 6 to reach the lower surface of said absorbent member 6, at least where the longitudinal marginal portions 11 of intermediate layer 10 extend beneath it.

Some of the liquid may therefore also be absorbed through the lower surface of absorbent member 6.

The liquid preferentially advances along the surface of intermediate layer 10 internally facing absorbent member 6, corresponding in the preferred embodiment to lower fibrous layer 15 of the layered structure in FIG. 3, so that it reaches it either by internal capillary diffusion through the fibres or from absorbent member 6, e.g. as a result of lateral losses from longitudinal lateral edges 8.

The low absorption capacity for liquid of the material from which intermediate layer 10 is constructed has the result that only a minimum quantity of liquid is retained within the said layer, the greater part being instead transmitted to absorbent member 6 in the ways described.

The hydrophobic external surface of intermediate layer 10 in the unperforated areas, or longitudinal marginal portions 11 and end zones 35, also has the further advantage of preventing capillary diffusion of the liquid beyond permeable hydrophilic portion 12. In this way the risk of the liquid migrating along the outer surface of intermediate layer 10 towards the lateral edges and beneath the absorbent member and towards end zones 35 corresponding to the anterior 2 and posterior 3 regions of absorbent towel 1 is reduced.

These areas in the external surface of intermediate layer 10 are therefore substantially unaffected by diffusion of the liquid and remain dry when in use, further limiting the possibility of losses from the lateral edges or ends of the absorbent.

Between absorbent member 6, which is partly or wholly surrounded by intermediate layer 10 at the surface facing the intimate clothing, and lower impermeable layer 7, there is preferably included a lower stopping layer 16. As shown in FIG. 1, lower stopping layer 16 is preferably shaped in the same way as sanitary towel 1 and therefore is wider than rectangular absorbent member 6, forming four portions 17 in the two anterior 2 and posterior 3 zones.

Lower stop layer 16 is preferably hydrophobic and has a very low capillary diffusion capacity. In a preferred configuration the said layer is formed by the said perforated layered structure which comprises intermediate layer 10, with the fibres of fibrous layers 13 and 15 being hydrophobic instead of hydrophilic.

Any small quantities of liquid which are absorbed by absorbent member 6 and subsequently released during use from the lower side facing the intimate clothing, in the case where intermediate layer 10 does not completely surround the absorbent member on that lower side, may be received from lower stop layer 16 within the small cavities formed by the holes and there retained without being able to diffuse elsewhere on account of the hydrophobic nature of the fibres making up that layer.

Also the four portions 17 of lower stop layer 16 which extend laterally with respect to longitudinal lateral edges of rectangular absorbent member 6 in the two anterior 2 and posterior 3 regions of shaped absorbent 1 confer greater consistency and thickness to the structure of absorbent 1 in these zones.

Absorbent member 6 may be obtained from a great variety of absorbent materials commonly used in sanitary towels, babies' nappies and other disposable absorbent articles.

Suitable materials may be cellulose fibres obtained from wood pulp, absorbent foams or sponges, synthetic fibres, hydrogelling absorbent materials or any material or combination of equivalent materials.

Hydrogelling absorbent materials, commonly called superabsorbents, are polymers which are capable of absorbing large quantities of liquid, in particular water, or, to a lesser extent even body fluids, by swelling. They also have the special property of retaining these fluids even under moderate pressure. Because of these properties they have for some time been proposed for use in combination with hydrophilic fibres in absorbent members intended for disposable absorbent articles.

The high absorbent capacity of superabsorbents is not however combined with a similarly high rate of absorption, and this may have an adverse effect on the performance of absorbent articles incorporating such substances.

Superabsorbents may in fact give rise to a phenomenon described in the prior art as "gel blocking". When a particle of superabsorbent is in contact with the liquid its external surface begins to absorb it and swells, obstructing the transmission of liquid into the said particle. The liquid can subsequently penetrate the core of the particle, which is still dry, only by means of a very slow diffusion mechanism.

This phenomenon may prevent full use being made of the high absorption capacities of superabsorbent substances.

The use of hydrogelling absorbent materials in all circumstances makes it possible to construct absorbent members containing a lesser quantity of hydrophilic fibres, for equal absorption capacity, which as a consequence are characterised by reduced dimensions and in particular reduced thickness in comparison with conventional absorbent members consisting of fibres alone.

Structures in which the fibres and particles of hydrogelling absorbent material are placed in separate superimposed layers, generally characterised by a highly reduced thickness, have been constructed.

Particularly preferred as an absorbent member for the sanitary towel according to this invention are the thin-layered absorbent structures described in PCT patent applications Ser. No. US93/06128 and US93/08597 and Italian Patent Application No. TO 93A 001028. [Note: This is DR55]

The said absorbent structures are generally formed of two or more fibrous layers, and between each pair of said fibrous layers there is an intermediate layer comprising particles of hydrogelling absorbent material and particles of thermoplastic organic polymer material. The fibrous layers extend laterally beyond the corresponding intermediate layers forming longitudinal marginal portions.

The fibrous layers which include the corresponding intermediate layers between them are joined together by fusing the particles of thermoplastic organic material and by means of continuous lines of adhesive which extend longitudinally at least along each longitudinal marginal portion.

Absorbent member 6 illustrated in cross-section in FIGS. 2 and 4' represents a preferred configuration of the thin layered absorbent structure described.

This absorbent member comprises a first fibrous layer 18, a second fibrous layer 19 and a third fibrous layer 20, and two intermediate layers 21 incorporating particles 22 of hydrogelling absorbent material and thermoplastic organic polymer material mixed together.

FIG. 2 illustrates continuous lines of adhesive 25 which extend longitudinally along the longitudinal marginal portions of the stratified structure located in the configuration illustrated along the longitudinal lateral edges 8 of absorbent member 6.

The fibrous layers which make up the layered absorbent structure illustrated in FIG. 2 are not identical. In particular the densities of the said layers decrease progressively from the first to the third fibrous layer.

Preferably the first and the second fibrous layers 18 and 19 comprise layers of short cellulose fibres constructed dry ("air laid"), while lower fibrous layer 20 is formed of cellulose fibres and synthetic fibres and is stabilised thermally ("thermobonded"). The presence of the synthetic fibres confers voluminous and elastic properties upon the layer. In use, upper layers 18 and 19, which are more dense, receive the liquid and are able to transmit it rapidly towards the underlying layers of fibre and hydrogelling absorbent material, at the same time distributing it in a longitudinal and transverse direction so as to increase the area of the underlying layers involved in absorption.

Lower fibrous layer 20, being more voluminous, has a smaller diffusion capacity but is able to accept a larger quantity of liquid within it, thus contributing to the overall absorption capacity of entire absorbent member 6 together with the particles of hydrogelling absorbent material in intermediate layers 21.

Furthermore, as a result of the elasticity conferred by the presence of synthetic fibres, it does not tend to collapse when it is wet. Any small quantities of liquid which might escape from lower fibrous layer 20 when the absorbent is subjected to normal pressures of use may nevertheless be reabsorbed by the particles of hydrogelling absorbent material in overlying intermediate layer 21.

In general the density of the fibrous layers forming absorbent member 6 preferably lies between 0.04 g/cm$^3$ and 0.20 g/cm$^3$ In an alternative configuration illustrated in FIG. 4', intermediate layer 10 may comprise longitudinal marginal portions 11 of a size such that they extend only partly along the side of absorbent member 6 facing the intimate clothing without over lapping as they do in FIG. 2.

In this case said intermediate layer 10 can be welded partly to itself along each end edge 38, in a similar way to that illustrated in FIGS. 1 and 3, and restricted to the two zones corresponding to longitudinal marginal portions 11 which are folded downwards, and at least partly to the immediately underlying layer, e.g. impermeable lower layer 7, or lower stop layer 16, in any event to close off absorbent member 6 at its two ends 34.

The alternative configuration illustrated in FIGS. 5 and 6 differs from that described above in that absorbent member 6 has a rectangular shape with straight end edges 38, with intermediate layer 10, which is also in this case longer than absorbent member 6, wrapped around it along lateral longitudinal edges 8 by means of longitudinal marginal portions 11, and also has end zones 35 folded beneath absorbent member 6 at its corresponding ends 34.

The folding of end zones 35 of intermediate layer 10 beneath absorbent member 6 at each respective end 34 may be performed before or after longitudinal marginal portions 11 are folded as illustrated in particular in FIG. 6.

Absorbent member 6 is thus completely surrounded by intermediate layer 10, which has substantially impermeable longitudinal marginal portions 11 and end zones 35 along longitudinal lateral edges 8 and end edges 38. In this way losses of liquid which might occur from the said edges while the absorbent is in use are prevented.

This configuration is particularly preferred where longitudinal marginal portions 11 of intermediate layer 10 are sufficiently wide to extend only partly along the side of absorbent member 6 facing the intimate clothing, as illustrated in cross-section in FIG. 4'. Alternatively, however, the marginal portions 11 may be long enough to meet one another in a butt joint, but not long enough to overlap one another.

FIGS. 7a and 7b show the steps involved in enclosing an absorbent member 6 with an intermediate layer 10. As can be seen, the size of the layer 10 is such that the longitudinal edges overlap one another at region 50, and the layer extends beyond the end edges 39 of the absorbent member. The end edges 36 of the layer 10, here shown as straight edges, are sealed together by a line of adhesive 37.

FIGS. 8a and 8b show the corresponding steps for the case where a layer 10 is of insufficient size to give an overlapping region 50, and where, indeed, the longitudinal edges of the layer 10 do not even meet one another.

A sanitary towel according to this invention may include embossed lines which involve only absorbent member 6 or the entire structure of sanitary towel 1, characterised in that they are substantially longitudinal in direction.

These embossed lines may be designed to aid diffusion of the liquid in a longitudinal direction within absorbent member 6, creating areas of local increased density in the structure, or representing lines of preferential folding so that the sanitary towel will adopt a preferred shape during use, e.g. a "W" shape, in order better to match the user's anatomy.

All the individual layers which form the structure of the sanitary towel according to this invention are preferably attached together, e.g. by means of adhesive.

Of course the details of this invention may be widely varied from those described or illustrated without detriment to its principles and without thereby going beyond the scope of this invention.

I claim:

1. An absorbent article comprising an upper layer which is permeable to liquids, a lower layer which is impermeable to liquids and an absorbent element located between the upper layer and the lower layer, the absorbent layer comprising two longitudinal side edges, two end edges, a surface facing the user's body and a surface facing the user's underclothing, at least the surface facing the body, the longitudinal side edges, and the two end edges being covered with an intermediate layer, the intermediate layer comprises a part which is substantially impermeable to liquids superposed on at least the side and end edges of the absorbent element, and a part which is substantially permeable to liquids at at least part of the surface of the absorbent element facing the body, the intermediate layer and lower layer together enveloping the absorbent layer in such a way as to prevent liquid leaking from any of its edges or the surface thereof facing the user's underclothing, wherein the intermediate layer has a bulk of more than 5 cm$^3$/g, a capillary diffusion capacity of less than 150 seconds for a length of 80 mm in the Horizontal Diffusion Test, and an absorption capacity of less than 1 g in the Free Absorption Test, both the tests being performed on a sample of material of the intermediate layer having a length of 80 mm and a width of 25.4 mm, using a 0.09% by weight saline aqueous solution.

2. An absorbent article according to claim 1, wherein the intermediate layer has a bulk of more than 7 cm$^3$/g.

3. An absorbent article according to claim 1, in which the material of the intermediate layer has an absorption capacity of less than 0.5 g.

4. An absorbent article according to any one of claim 1, wherein the intermediate layer comprises a layered structure formed of a film which is impermeable to liquids and of a non-woven fabric material, the non-woven fabric material forming a layer having a capillary diffusion capacity in the inner surface of the intermediate layer.

5. An absorbent article according to claim 4, wherein the intermediate layer has a three layer structure, comprising a central polyethylene film and two outer polypropylene fibrous layers.

6. An absorbent article according to claim 4, wherein the portion which is permeable to liquids, of the intermediate layer comprises perforations.

* * * * *